(12) United States Patent
Waller

(10) Patent No.: US 6,280,980 B1
(45) Date of Patent: Aug. 28, 2001

(54) PROCESS FOR THE PRODUCTION OF L-ASPARTIC ACID

(75) Inventor: Andrew Stuart Waller, Ballwin, MO (US)

(73) Assignee: Solutia Inc., St. Louis, MO (US)

(*) Notice: Subject to any disclaimer, the term of this patent is extended or adjusted under 35 U.S.C. 154(b) by 0 days.

(21) Appl. No.: 09/297,356

(22) PCT Filed: Oct. 31, 1997

(86) PCT No.: PCT/US97/19594

§ 371 Date: Apr. 30, 1999

§ 102(e) Date: Apr. 30, 1999

(87) PCT Pub. No.: WO98/20147

PCT Pub. Date: May 14, 1998

Related U.S. Application Data

(60) Provisional application No. 60/030,724, filed on Nov. 8, 1996.

(51) Int. Cl.$^7$ ................................................ C12P 13/20
(52) U.S. Cl. ................................................ 435/109
(58) Field of Search ............................. 435/109

(56) References Cited

U.S. PATENT DOCUMENTS

| | | | |
|---|---|---|---|
| 3,391,059 | 7/1968 | Takamura et al. | 195/30 |
| 4,560,653 | 12/1985 | Sherwin et al. | 435/109 |
| 5,541,090 | 7/1996 | Sakano et al. | 435/109 |
| 5,741,681 | * 4/1998 | Kato et al. | 435/109 |
| 5,783,428 | * 7/1998 | Goto et al. | 435/145 |

FOREIGN PATENT DOCUMENTS

| | | |
|---|---|---|
| 0683231 | 11/1995 | (EP) . |
| 0693557 | 1/1996 | (EP) . |
| 0752476 | 1/1997 | (EP) . |

OTHER PUBLICATIONS

Kimura, Takuhei; Kawabata, Yasuro and Sato, Eiji "Enzymatic Production of L–Malate from Maleate by Alcaligenes sp.", *Agric. Biol. Chem.*, 1986, vol. 50, pp. 89–94.

Takamura, Yoshichika; Kitamura, Iwao; Iikura, Minoru; Kono, Kageaki; Ozaki, Asaichiro "Studies of the Enzymatic Production of L–Aspartic Acid from Maleic Acid", *Agric. Biol. Chem.*, 1966, vol. 30, No.4 pp. 338–344.

Otsuka, Ken'ichi "Cis–trans Isomerase Isomerisation from Maleic Acid to Fumaric Acid" *Agric. Biol. Chem.*, (1961) vol. 25, No.,9 pp. 726–730.

Chemical Abstracts—1996. Vol. 125, No. 23, pp. 1079–1080.

* cited by examiner

Primary Examiner—Herbert J. Lilling
(74) Attorney, Agent, or Firm—Lathrop & Gage LC

(57) ABSTRACT

A process for production of L-aspartic acid comprising (1) contacting (A) an enzyme-containing material having maleate isomerase activity and aspartase activity, or (B) an enzyme-containing material having maleate isomerase activity and an enzyme-containing material having aspartase activity, with an aqueous substrate solution containing maleic acid and ammonia, and/or mono or di-ammonium maleate, to form L-ammonium aspartate, in a reaction solution, (2) adding the reaction solution to an aqueous solution of maleic acid or maleic anhydride at a controlled rate to crystallize L-aspartic acid in a mother liquor, and (3) recovering the L-aspartic acid from the mother liquor, and (4) optionally recycling said mother liquor as a substrate solution for further reaction with said enzyme containing material of Step 1 and (5) optionally adding alkali such as ammonia to said mother liquor before, during, or after recycle.

13 Claims, No Drawings

PROCESS FOR THE PRODUCTION OF L-ASPARTIC ACID

This Application is a 371 of PCT/U.S. 9719594 which claims priority to Provisional U.S. Ser. No. 60/030,724 filed Nov. 8, 1996.

The present invention relates to a process for the production of L-aspartic acid.

BACKGROUND OF THE INVENTION

Various processes for production of L-aspartic acid from fumaric acid and ammonia (to create diammonium fumarate) using microorganisms having aspartase activity have been published. For example see—Chibata, I; Tosa, T.; Sato, T. *Comprehensive Biotechnology Vol.* 3 Ed. Murray Moo-Young, Permagon, 1985. In these published processes, the L-aspartic acid is usually recovered by precipitation of L-aspartic acid crystals resulting from the addition of a mineral acid such as sulfuric acid to the reaction solution, and separation of the crystals. However in these published processes, a large amount of waste salt(s), such as ammonium sulfate, is generated as a by-product of the precipitation. The production of these salts is undesirable from an environmental perspective and causes the undesirable loss of ammonia.

U.S. Pat. No. 4,560,653 ('653) issued Dec. 24, 1985, discloses a process for the production of L-aspartic acid wherein aspartase or an aspartase-producing microorganism acts upon fumaric acid and ammonia. L-aspartic acid is precipitated by addition of maleic acid and filtered from the solution and the mother liquors are recycled. This '653 patent discloses the use of a chemical catalyst for maleic acid to fumaric acid isomerization.

As an alternative catalyst for maleate to fumarate isomerization, enzyme-containing organisms with maleate isomerase activity can be used. For examples see—Otsuka, K. *Agr. BioL. Chem.*, 25(9), 1961, 726.—Scher, W. and Jakoby, W. B. *J. Biol. Chem.*, 244(7), 1969, 1878. This catalyst reportedly gives high conversions of maleic acid salts to fumaric acid salts at basic pH.

U.S. Pat. No. 3,391,059 which issued Jul. 12, 1968, discloses an enzyme containing organism with maleate isomerase activity and aspartase activity to produce L-aspartic acid directly from maleic acid.

The art of preparing L-aspartic acid economically and efficiently with minimal or no environmental adverse impact continues to be of interest to industry.

OBJECTS OF THE INVENTION

It is an object of this invention to provide a highly efficient process for the production of L-aspartic acid using inexpensive starting substrates.

It is another object of this invention to provide a highly efficient process for the production of L-aspartic acid with minimal generation of ammonium salt as a by-product.

It is a still further object of this invention to provide a process for the production of L-aspartic acid having an improved yield while generating a minimum of an undesired side product.

These and other objectives are met in this invention which is hereinafter described in more detail.

BRIEF SUMMARY OF THE INVENTION

In the broadest aspect of this invention and in a preferred embodiment, L-ammonium aspartate is produced from maleic acid or maleic anhydride by enzymes or microorganisms. L-aspartic acid is preferably recovered by precipitation using maleic acid. An added benefit is that optionally the mother liquor can be recycled for reuse after recovering L-aspartic acid from the reaction solution. Optionally the pH of the mother liquor may be made basic.

This invention comprises a process for the production of L-aspartic acid comprising the steps of (1) contacting (A) an enzyme-containing material having maleate isomerase activity and aspartase activity, or (B) an enzyme-containing material having maleate isomerase activity and an enzyme-containing material having aspartase activity, with an aqueous substrate solution containing maleic acid and ammonia, and/or mono or di-ammonium maleate or mixtures thereof to form L-ammonium aspartate in a reaction solution, (2) adding said reaction solution at a controlled rate to an aqueous solution of maleic acid or aqueous slurry of maleic anhydride to crystallize L-aspartic acid in a mother liquor and (3) recovering said L-aspartic acid from said mother liquor, and (4) optionally recycling said mother liquor as a substrate solution for further reaction with said enzyme containing material of Step (1) above and (5) optionally adding ammonia or other alkali to said mother liquor before, during or after recycle.

In another preferred embodiment of this invention, a substrate solution at a temperature from about 10 C. to about 60 C. containing maleic anhydride, maleic acid and salts thereof and ammonia, or ammonium maleate wherein the molar ratio of ammonia to maleic acid is from about 1 to about 2 is contacted with microbial cells having both maleate isomerase activity and aspartase activity, or with microbial cells having maleate isomerase activity and microbial cells having aspartase activity, or alternatively disrupted cells or enzymes thereof or the equivalent thereof.

An enzyme-containing material such as microbial cells having maleate isomerase activity and an enzyme-containing material having aspartase activity may be used as a mixture if desired. Without being bound by theory it is believed that maleate isomerase-containing material converts ammonium maleate to ammonium fumarate, and then aspartase-containing material converts the ammonium fumarate to L-ammonium aspartate. These conversions preferably occur in the same vessel or container so as to minimize the concentration of fumarate salt formed during the reaction. When the activity of the prior-used enzyme-containing material decreases, preferably it may be totally or partially replaced with fresh species.

The ratio of maleate isomerase containing enzyme to aspartase enzyme may be adjusted. Preferably, the activity of the aspartase enzyme is sufficiently high to minimize any appreciable fumarate concentration being formed during the reaction. Highest yields of aspartate are believed to occur when the fumarate concentration is suppressed since it is believed to inhibit maleate isomerase activity.

L-ammonium aspartate is formed during the reaction and the resulting solution is added to a slurry of maleic anhydride or a solution of maleic acid at a controlled rate to crystallize L-aspartic acid. The L-aspartic acid crystals are separated from the solution. The recovered crystals are washed with water to reduce the amount of maleic acid and/or salt thereof. As used herein, the term "controlled rate" means the gradual addition i.e., addition in a controlled manner of the reaction solution to the maleic acid or maleic anhydride in order to minimize the formation of reaction byproducts and result in an increased yield of L-aspartic acid.

The mother liquor from which the crystals have been removed is preferably recycled and reused as a substrate solution for further production of more L-aspartic acid. If this optional step is carried out, it reduces raw material cost and avoids generating waste water containing significant ammonia which heretofore required disposal at a potential detriment to the environment.

In the process of this invention, maleic anhydride is used preferably as one of the starting materials to produce L-aspartic acid. The mother liquor may be recycled as the substrate solution without addition of chemical catalyst. The complete recycle of the soluble mother liquor results in very efficient production with minimal or zero waste and minimal ammonia usage. Thus, L-aspartic acid can be produced cheaply and efficiently.

DETAILED DESCRIPTION OF THE INVENTION

Without being bound by theory, illustrations of some chemical reactions believed to occur in parts of this process are shown in a Table below. Some steps are optional. Some steps occur to a greater or a lesser degree.

TABLE

| Step | Action | Chemistry |
|---|---|---|
| 1 | Maleate Isomerase Enzymatic Maleate to Fumarate Isomerization | Diammonium Maleate → (Maleate Isomerase Enzyme) → Diammonium Fumarate |
| 1 | Aspartase Enzymatic Conversion of Fumarate to Aspartate | Diammonium Fumarate → (Aspartase Enzyme) → Ammonium L-Aspartate |
|  | Dissolution of Maleic Anhydride | Maleic Anhydride + $H_2O$ → Maleic Acid |
| 2 | Acidification and precipitation of L-aspartic acid | Ammonium L-Aspartate · Maleic Acid → L-Aspartic Acid · Ammonium Maleate |

TABLE-continued

| Step | Action | Chemistry |
|---|---|---|
| 3 & 4 | Filtration of precipitated L-aspartic acid Recycle mother liquor containing ammonium maleate | |
| 5 | Neutralization of ammonium maleate to form diammonium maleate | 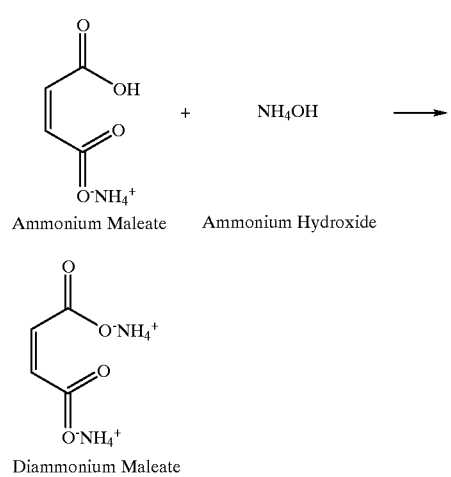 Ammonium Maleate + NH₄OH → Ammonium Hydroxide<br><br>Diammonium Maleate |
| | Go Back to Step 1 optional | |

Any suitable microorganism having maleate isomerase activity and aspartase activity can be used. Typical non-limiting illustrative enzymes include *Pseudomonas fluorescence, Alcaligenese faecalis, Pseudomonas ovalis, Aerobacter aerogenes, Escherichia coli, Brevibacterium guale, Brevibacterium vitarumen, Achromobacter liquenfaciens, Bacillus brevis*, mixtures thereof and the like.

In addition, a combination of a microorganism having maleate isomerase activity and a microorganism having aspartase activity can be employed if desired.

Illustrative but non-limiting examples of microorganisms which have maleate isomerase activity which may be suitably employed herein include those which convert maleic acid to fumaric acid such as the genus Pseudomonas including *Pseudomonas fluorescence*. Other illustrative suitable enzymes include without limitation *Alcaligenese faecalis, Escherichia coli, Bacillus brevis*, mixtures thereof and the like.

Examples of suitable illustrative non-limiting microorganisms useful herein are those having aspartase activity that convert fumaric acid to L-aspartic acid. These include the genus Escherichia such as *Escherichia coli* ATCC 11303 as well as microorganisms belonging to the genus Brevibacterium.

Any method of enzyme cultivation or manufacture for use in this invention may be employed. Conventional fermentation techniques and conventional media can be used. The enzyme may be employed as an enzyme broth, a whole cell, a disrupted cell, or an encapsulated enzyme or cell, mixtures thereof and the like.

The reaction is preferably carried out after enzymes that interfere with the reaction for L-aspartic acid production are inactivated or substantially inactivated. For example, the enzyme-containing material may be heated to about a temperature from about 40 C. to 60 C. and more preferably from about 50° C. to 58 C. Such temperatures may be employed in the presence of L-aspartic acid and ammonium ion to inactivate Fumarase enzyme.

It is preferable that the enzymatic reactions be carried out in the same vessel or container or tank, as the fumarate formed by the maleate isomerase has a tendency to inhibit maleate isomerase activity. Preferably, although not required, steps (1a) or (1b) are performed at the same time or somewhat close in time or in the same tank as carrying out these steps in this desired manner increases yields substantially. Without being bound by theory it is believed that it is important to keep the aspartase enzyme activity high, so that the fumarate concentration during the reaction is minimized.

The substrate solution in the present invention is preferably selected from the group consisting of maleic anhydride, maleic acid, salts of maleic acid, mixtures thereof and the like. In the present invention, the ammonia may be gaseous ammonia or aqueous ammonia solution for ease of handling. The concentration of aqueous ammonia solution is not critical; however, more concentrated solution is typically desirable to minimize water in the recycle stream.

Typically the pH of the enzyme substrate solution is from about 5 to about 10, preferably from about 7 to about 9, and most preferably from about 8 to about 9. The pH can be adjusted using alkali bases, but ammonia is preferred. When maleic acid or salts thereof and ammonia are mixed, the mixing can be carried out in any convenient manner. The minimum quantities of water should be added in this process since it must be removed to maintain constant or nearly constant concentration throughout the process.

A preferred substrate solution containing maleic acid and ammonia is preferably prepared with water and a tromethamine (TRIS) or phosphate buffer. The concentration of maleic acid is preferably in the range from about 0.1 M to about 3.5 M although greater or lesser concentrations may be employed if desired. The concentration of maleic acid is more preferably from about 1 to about 2 M.

To increase maleate isomerase enzyme catalyst activity, a compound containing a reducing SH group including but not limited to 2-mercaptoethanol, thioglycerol, or a substantial equivalent thereof or the like, is preferably added in a concentration from about 0.1 to about 100 mM, and more preferably from about 1 to about 25 mM to increase maleate isomerase enzyme catalyst activity.

Any conventional reactor such as a continuous stirred tank, column-type reactor or the like may be employed in the invention process. In case of column-type reactor, flow rate can be changed dependent on the kind and activity of enzyme-containing product contained in the column.

Reaction temperature for the enzyme reaction(s) is usually from about 10 to about 60 C. and preferably from about 25 to about 40 C. although greater or lesser temperatures may be employed if desired.

In a preferred embodiment, after enzymatic reaction of maleic acid and ammonia to form L-ammonium aspartate, the reaction solution is added at a controlled rate to an aqueous slurry of maleic anhydride or a solution of maleic acid to crystallize L-aspartic acid and to recover the same.

Optional recycle of mother liquor is possible by using maleic acid or maleic anhydride to crystallize L-aspartic acid. If a mineral acid is used to crystallize L-aspartic acid, ammonium salt of the mineral acid is formed which cannot be used as an enzyme substrate. The mother liquor obtained when a mineral acid is used is usually then discarded as waste.

In this invention, the term "maleic acid" as used to in the context of crystallizing L-aspartic acid includes without limit maleic anhydride, maleic acid or salts of maleic acid, mixtures thereof and the like. Maleic acid can be an aqueous solution or slurry—but preferably is that formed by reacting maleic anhydride in water. Due to the need to achieve water balance in the process, minimum quantities of water are preferably added in this process since it must be removed to maintain constant or nearly constant concentration throughout the process.

The total amount of maleic acid employed to crystallize L-aspartic acid can vary and depends on the total amount of L-aspartic acid (present as a salt) in the reaction solution. The amount of maleic acid employed for acidifying the L-aspartate present in the reaction solution is preferably at about equimolar to the total L-ammonium aspartate for efficient and multiple recycle of the mother liquor although the concentrations may be different. Preferably, the maleic acid is at a higher concentration than the L-aspartic salt. A desired mole ratio of maleic acid to L-ammonium aspartate is preferably from about 0.5 to about 1.5 and most preferably from about 0.95 to about 1.2 although greater and lesser ratios may be employed if desired.

However, if lesser maleic acid than above noted is added, the yield of L-aspartic acid recovered (as crystals) is lower while if more than the amount is used, by-products other than L-aspartic acid may be produced. In addition, excess maleic acid causes excess generation of substrate with each optional recycle in the process.

When maleic anhydride is added to the L-ammonium aspartate reaction solution, maleamic acid is formed, usually in the range from about 2% to about 5%. This is an undesirable by-product that hampers efficient recycle of ammonium maleate. The maleamic acid formed is sufficiently water soluble that it remains in the mother liquor and is not converted into useful product by enzymatic action.

If L-ammonium aspartate is added to maleic acid or maleic anhydride at a controlled rate, a significantly lesser amount and possibly no maleamic acid is formed. The use of maleic anhydride during crystallization is desirable due to its ease of use and reduced cost. Thus adding the reaction solution to the aqueous maleic acid solution at a controlled rate avoids forming undesirable maleamic acid.

Preferably the reaction solution is gradually added to the maleic acid solution or slurry of maleic anhydride to crystallize L-aspartic acid. More preferably a controlled method of addition is employed to achieve the benefits of this invention. The crystal particle size can be controlled through variables such as crystallization temperature, agitation speed, sonitication, seeding, and rate of addition of the reaction solution to the maleic acid and the like techniques which will be apparent to those of skill in the art after reading this specification.

Crystallization of L-aspartic acid can be carried out from about 0 C. to about 100 C. for about 10 minutes to about 24 hours and preferably from about 5 C. to about 60 C. for about 30 minutes to about 2 hours although greater or lesser temperatures and greater or lesser times may be employed if desired.

The L-aspartic acid crystals are separated from the mother liquor by any conventional separation method such as centrifugation, filtration and the like known to those of skill in the art. If desired, the crystals may be washed according to conventional wash procedures. The unwashed crude crystals of the L-aspartic acid usually contain from about 5% to about 15% by weight of maleic acid or salts thereof and this can be decreased by washing with water if desired.

This wash water is preferably used as makeup water for forming the maleic acid used to precipitate the L-aspartic acid. This wash water can also be mixed with the mother liquors from which L-aspartic acid crystals have been separated or a combination of both. The wash water may be concentrated prior to the mixing with the mother liquor.

L-aspartic acid crystals containing about 0.01 to about 15% by weight (unwashed) and preferably from about 0.01 to about 1% by weight (washed) of maleic acid and/or salts thereof is preferably produced, having an average crystal size controlled by changing the crystallization conditions. An average particle size of from about 15 to about 500 mm is obtained, with a desirable "flat plate" crystal habit although this is not critical.

L-aspartic acid product is industrially useful, for example, as a starting material or intermediate for forming surfactants, metal ion sequestrants, detergent compositions, cosmetic compositions, pharmaceuticals, coatings, and the like. In addition, it is used as a starting material for the production of industrially useful polymers such as poly(aspartic acid) and its derivatives thereof as well as a food additive.

If desired, the mother liquor from which L-aspartic acid has been separated can be used as the substrate solution for further production of L-aspartic acid. Wash water from washing crude L-aspartic acid crystals can be mixed with the mother liquor. Maleic acid, maleic anhydride and maleic acid salts may be added to the mother liquor to adjust maleic acid concentration in the mother liquor. Ammonia may be added to adjust the molar ratio of ammonia to maleic acid preferably in the range from about 1 to about 2 mole equivalents. Water may also be added or removed to adjust the volume of recycled mother liquor to that of the previous substrate solution if desired. The cycles collectively comprising (1) reaction of maleic acid and ammonia with microbial cells or disrupted cells, (2) crystallization of L-aspartic acid, (3) separation and washing of L-aspartic acid and (4) optional recycle of the mother liquor can be repeated over and over according to the process of this invention.

Optionally an alkali such as ammonia, ammonium hydroxide, an alkali metal hydroxide, alkaline earth metal hydroxide or any compatible base, mixtures thereof and the like may be added to the mother liquor. Ammonia is preferably added to the mother liquor from about 0.5 to about 1.0 mole equivalents based on the amount of maleic acid used to precipitate the L-aspartic acid. Typically about 0.6 to about 0.7 mole equivalents would be employed to bring the pH into the more preferable range of about 8 to about 9. When the amount of added ammonia is less than about 0.5 equivalents, the pH of the substrate solution may be too low for efficient and complete conversion by the enzyme(s).

If desired, ammonia may be preferably added to the mother liquor to create a desirable substrate for the enzyme (s) and to prolong the enzyme activities of microbial cells or disrupted cells or enzymes for as long as possible. Preferably, ammonia is added to the is mother liquor to maintain a pH of the solution from about 6 to about 9 and more preferably from about 8 to about 9 although greater or lesser pH values may be employed.

Batch and continuous operations and variations thereof are envisioned as processes of this invention without limitation. An effective amount of the composition(s) of this invention and of the components of such composition(s) is preferably employed in achieving the benefits of this invention.

The following EXAMPLES are intended to provide detail about this invention and are not meant to limit this invention in any way.

EXAMPLES

Example 1

Maleic anhydride (45.54 g or 0.46 mole) was dissolved in water (29.66 g) to form a solution. This solution was then heated from room temperature to 60 C. A total of 279.63 g of 24.2% (w/w) solution of L-ammonium aspartate solution (0.45 mole of L-ammonium aspartate) was metered at a controlled rate over a 30 minute time period with stirring. After stirring for 90 minutes at 60 C., the solution was cooled to 6 C. in an ice water bath. The final pH of the solution was 4.1. L-aspartic acid crystals were recovered using filtration and washed with 67.35 g of water. The final yield of L-aspartic acid crystals after washing was 96% (57.24 g, 0.43 mole).

Example 2

Maleic anhydride (48.14 g or 0.49 mole) was slurried in water (69.63 g).

The temperature of the solution was 32 C. A total of 311.25 g of 24.2% (w/w) solution of L-ammonium aspartate solution (0.50 mole of L-ammonium aspartate) was added at a controlled rate over a 30 minute time period with stirring. After stirring for 90 minutes at 35 C., the solution was cooled to 9 C. The final pH of the solution was 4.4. L-aspartic acid crystals were recovered using filtration and washed with 82.33 g of water. The final yield of L-aspartic acid crystals after washing was 100+% (69.01 g, 0.52 mole).

Example 3 Comparative Example

Maleic anhydride (53.75 g or 0.548 mole) was added to a 24.2% L-ammonium aspartate solution in water 369.40 g or 0.595 mole) at 60 C. After stirring for 90 minutes at 60 C., the solution was cooled to 9 C. The final pH of the solution was 3.9. L-aspartic acid crystals were recovered using filtration, the crystals were not washed. The final yield of L-aspartic acid crystals was 88.2% (64.33 g, 0.48 mole). Proton NMR of the mother liquor confirmed the presence of maleamic acid. Comparing the results of Examples 1 and 2 to Comparative Example 3 shows that the practicing the process of this invention results in increased yields.

Example 4

The mother liquor from L-aspartic acid crystallization comprised primarily of ammonium salts of maleic acid in water, approximately 1–2M in concentration (372.92 g) was treated with 33.81 g of 29.7% aqueous ammonia (0.28 mole). The starting pH of the mother liquor prior to ammonia addition was 4.2. The final pH of the solution was 8.4. The solution was a mixture of diammonium maleate and ammonium maleate salts.

Example 5

This Example shows maleate isomerase reaction. Approximately 250 microliters of the diammonium maleate solution from Example 4 was diluted with water, Tromethamine buffer (to give 50 mM) and 2-mercaptoethanol (to give 4.9 mM) and 50 ml of maleate isomerase enzyme broth. The final maleate substrate concentration was 100 mM. The solution was stirred at about 25 C. for 2 hours. The tube contents were then separated from the enzyme by centrifugation through an Amicon Centricon-10, a 10,000 MW cut-off filter, using a Sorvall RT 6000B refrigerated centrifuge. All operations in the centrifuge were performed at about 4 C. The yield of diammonium fumarate, as measured by HPLC, was 100%.

Example 6

Approximately 250 microliters of the diammonium maleate solution from Example 4 was diluted with water, Tromethamine buffer (to give 55 mM) and 2-mercaptoethanol (to give 5.5 mM) and 100 ml of maleate isomerase enzyme broth. The final maleate substrate concentration was 111 mM. Several encapsulated beads containing aspartase enzyme were also added to the solution. The solution was stirred at 25 C. for 30 minutes. The tube contents were then separated from the enzyme containing materials by centrifugation through an Amicon Centricon-10, a 10,000 MW cut-off filter, using a Sorvall RT 6000B refrigerated centrifuge. All operations in the centrifuge were performed at 4 C. The yield of L-aspartic acid, as measured by HPLC, was 83.7%.

Example 7

*Pseudomonas fluorescens* was allowed to grow using the method from Scher and Jakoby. The cultured cells were then suspended in a buffer of 0.1 M potassium phosphate containing 5 mM of 2-mercaptoethanol. The cells were lysed with a French press and centrifuged. The suppressant fluid was washed with the buffer solution and heated at 58 C. for 7 hours. The supernatant was then cooled to 4 C., centrifuged, treated with streptomycin sulfate, and centrifuged again. The supernatant was then treated with ammonium sulfate (up to 53% w/w). The resulting precipitate was dissolved in 0.03 M tromethamine buffer with 5 mM 2-mercaptoethanol. This maleate isomerase enzyme broth was then used for Examples 5–6 above.

Although the invention has been described in terms of specific embodiments which are set forth in considerable detail, it should be understood that this description is by way of illustration only and that the invention is not necessarily limited thereto, since alternative embodiments and operating techniques will become apparent to those skilled in the art (in view of the disclosure). Accordingly, modifications are contemplated which can be made without departing from the spirit of the described invention.

What is claimed is:

1. A process for production of L-aspartic acid comprising the steps of (1) contacting (A) an eznzyme-containing material having maleate isomerase activity and aspartase activity, or (B) an enzyme-containing material having maleate isomerase activity and an enzyme-containing material having aspartase activity, with an aqueous substrate solution containing maleic acid and ammonia, and/or mono or di-ammonium maleate, to form L-ammonium aspartate in a reaction solution, (2) adding said reaction solution to an aqueous solution of maleic acid or maleic anhydride at a controlled rate to crystallize L-aspartic acid in a mother liquor, and (3) recovering said L-aspartic acid from said mother liquor.

2. The process of claim 1, wherein said mother liquor is recycled as a substrate solution for reaction with said enzyme comtaining material(s) of Step 1.

3. The process of claim 2, wherein the pH of said mother liquor is adjusted before, during or after recycle.

4. The process of claim 2, wherein the pH is adjusted and said mother liquor is recycled.

5. The process of claim 4, wherein an amount of alkali is added to the mother liquor sufficient to provide about 1.5 to about 2.0 mole equivaients relative to maleic acid and the mother liquor is recycled as the substrate solution.

6. The process of claim 5, wherein said alkali is ammonia or ammonium or mixtures thereof.

7. The process of claim 4, wherein the pH of the mother liquor is adjusted to a pH in the range from about 6 to about 9 and the mother liquor is recycled as the substrate solution.

8. The process of claim 7, wherein said pH is in the range from about 8 to about 9.

9. A process according to claim 1, wherein the enzyme-containing material having maleate isomerase activity and an enzyme-containing material having aspartase activity, are brought into contact with a substrate solution containing maleic acid and ammonia, and/or mono or di-ammonium maleate, to form L-ammonium aspartate in the same tank or at the same time so as to reduce the instantaneous concentration of fumaric acid salts or fumaric acid.

10. A process according to claim 1, wherein the enzyme-containing material having maleate isomerase activity and aspartase activity, the enzyme-containing material having maleate isomerase activity, and the enzyme-containing material having aspartase activity are microbial cells, disrupted cells or enzymes, or are immobilized material containing microbial cells, disrupted cells or enzymes.

11. The process of claim 1, wherein the amount of maleic anhydride and/or maleic acid used to acidify the reaction solution is from about 0.5 to about 1.5 mole equivalents relative to the amount of L-aspartic acid present in the reaction solution.

12. A process according to claim 11, wherein the amount of maleic anhydride and/or maleic acid is in the range from about 0.95 to about 1.2 mole equivalents relative to the amount of L-aspartic acid present in the reaction solution.

13. A process according to claim 1, wherein L-aspartic acid crystals are washed with water, the wash water is used as the make up water for the maleic acid solution or maleic anhydride and/or the wash water is mixed with the mother liquor from which L-aspartic acid has been removed and the mixture is recycled as the substrate solution.

* * * * *